United States Patent [19]

Pariza et al.

[11] Patent Number: 5,075,289
[45] Date of Patent: Dec. 24, 1991

[54] 9-R-AZACYCLIC ERYTHROMYCIN ANTIBIOTICS

[75] Inventors: Richard J. Pariza, Winthrop Harbor; Paul A. Lartey, Wadsworth; Clarence J. Maring, Libertyville; Larry L. Klein, Lake Forest, all of Ill.

[73] Assignee: Abbott Laboratories, Abbott Park, Ill.

[21] Appl. No.: 203,400

[22] Filed: Jun. 7, 1988

[51] Int. Cl.$^5$ .................. A61K 31/70; C07H 17/08
[52] U.S. Cl. .................. 514/29; 536/7.2; 536/7.4
[58] Field of Search .................. 536/7.2, 7.4; 514/29

[56] References Cited

U.S. PATENT DOCUMENTS

| | | | |
|---|---|---|---|
| 3,574,185 | 4/1971 | Tamburasey et al. | 536/7.2 |
| 3,652,537 | 3/1972 | Massey et al. | 536/7.4 |
| 3,660,376 | 5/1972 | Massey et al. | 536/7.4 |
| 3,681,322 | 8/1972 | Kitobell et al. | 536/7.4 |
| 3,780,019 | 12/1973 | Wildsmith | 536/7.4 |
| 3,780,020 | 12/1973 | Evans et al. | 536/7.4 |
| 3,790,559 | 2/1974 | Wildsmith | 536/7.4 |
| 3,794,635 | 2/1974 | Evans et al. | 536/7.4 |
| 3,923,784 | 12/1975 | Kierstead et al. | 536/7.4 |
| 3,928,387 | 12/1975 | Kierstead et al. | 536/7.4 |
| 3,939,144 | 2/1976 | Radoboija et al. | 536/7.4 |
| 3,983,103 | 9/1976 | Kobrehel et al. | 536/7.4 |
| 3,992,264 | 11/1976 | Kierstead et al. | 435/7.5 |
| 4,016,263 | 4/1977 | Wetzel et al. | 514/29 |
| 4,048,306 | 9/1977 | Maier et al. | 514/29 |
| 4,070,376 | 1/1978 | LeMahien et al. | 536/7.4 |
| 4,256,738 | 3/1981 | Woitum et al. | 514/29 |
| 4,283,527 | 8/1981 | Sciavolino et al. | 536/7.4 |
| 4,328,334 | 5/1982 | Kobrehel et al. | 536/7.4 |
| 4,349,545 | 9/1982 | d'Ambrieres | 514/29 |
| 4,465,674 | 8/1984 | Bright et al. | 536/7.4 |
| 4,492,688 | 1/1985 | Bright | 514/29 |
| 4,512,982 | 4/1985 | Hauske et al. | 514/29 |
| 4,518,590 | 5/1985 | Nauske et al. | 514/29 |
| 4,668,776 | 5/1987 | Yamada et al. | 536/7.4 |
| 4,670,549 | 6/1987 | Morimoto et al. | 536/7.4 |
| 4,680,386 | 7/1987 | Morimoto et al. | 536/7.4 |
| 4,847,242 | 7/1989 | Davies | 514/29 |

FOREIGN PATENT DOCUMENTS

| | | | |
|---|---|---|---|
| 109253 | 5/1984 | European Pat. Off. | 536/7.4 |
| 136831 | 4/1985 | European Pat. Off. | 536/7.4 |
| WO86/01513 | 3/1986 | European Pat. Off. | 514/29 |
| 194833 | 9/1986 | European Pat. Off. | 514/29 |
| 201166 | 11/1986 | European Pat. Off. | 536/7.4 |
| 216169 | 4/1987 | European Pat. Off. | 536/7.4 |
| 238178 | 9/1987 | European Pat. Off. | 536/7.4 |
| 0260938 | 3/1988 | European Pat. Off. | 536/7.4 |
| 2534588 | 4/1984 | France | 536/7.4 |

Primary Examiner—Elli Peseley
Attorney, Agent, or Firm—Steven F. Weinstock; Andreas M. Danckers

[57] ABSTRACT

Semisynthetic antibiotics with improved therapeutic properties are disclosed. In particular, 9-R-azacyclic derivatives of erythromycin, its derivatives, and their salts and esters show superior antimicrobial activity compared to other macrolide compounds.

9 Claims, No Drawings

9-R-AZACYCLIC ERYTHROMYCIN ANTIBIOTICS

TECHNICAL FIELD

This invention relates to antibiotics for use in the chemotherapy of antimicrobial infections and, more particularly, to erythromycin derivatives which exhibit high antimicrobial activity and improved therapeutic ratios.

BACKGROUND ART

Erythromycin and common derivatives are widely used and exhibit desirable activity against a number of gram-positive pathogens. Since some pathogens are less susceptible than others to these drugs, high doses of these antibiotics are occasionally necessary in the treatment of serious or widespread infections. As with all drugs, toxic effects are sometimes observed at higher dosage levels, particularly in patients who are seriously compromised by infection and thus are most in need of treatment. Unfortunately, improvements in potency and spectrum are often accompanied by an increase in toxicity, so that later generation drugs usually represent a compromise between these competing considerations. As a result, there is a continuing search for antibiotics which are more potent against certain organisms, or, preferably, against all organisms, than those currently used. Desirably, such drugs will have an improved therapeutic ratio, which is the ratio of the effective therapeutic or prophylactic dose to the toxic dose, usually expressed in terms of the $ED_{50}/LD_{50}$ ratio.

It is an object of this invention to provide novel compounds which are derivatives of erythromycin, and which have greater in vitro and in vivo potency than erythromycin against certain organisms, and increased therapeutic ratios in comparison to erythromycin.

This and other objects of this invention will be more fully understood by reference to the following disclosure.

Disclosure of the Invention

This invention provides novel erythromycin A 9-R-azacyclic compounds and pharmaceutically acceptable salts and esters thereof. In structural terms, this invention provides compounds of the formula

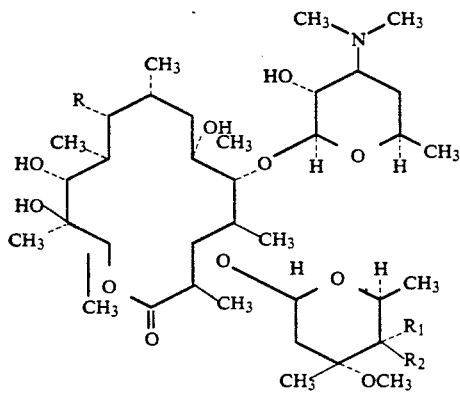

wherein $R_1$ is hydrogen, OH, carbamoyloxy or $NR_3R_4$ wherein $R_3$ and $R_4$ are independently selected from H and loweralkyl; $R_2$ is hydrogen when $R_1$ is other than hydrogen or $R_2$ is $NR_3R_4$ when $R_1$ is hydrogen; and R is a heterocyclic of the formula:

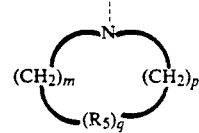

wherein m is 1–3, q is 0 or 1, p is 1–2 and $R_5$ is selected from $CH_2$, O, S, C=O, C=S, $SO_2$, SO, —CH=CH—, CH(OH)CH(OH), NH and $CR_6R_7$ wherein $R_6$ and $R_7$ together form an ethylenedioxy bridge; or R is a heterocyclic as defined above having substituents selected from loweralkyl, hydroxy, loweralkoxy, halo, phenyl, loweralkanoyl, benzoyl, benzyloxycarbonyl, t-butyloxycarbonyl, arylalkoxyalkyloxy and alkoxyalkyloxy; or R is 4,4 tetramethylenepiperidine, 4,4 pentamethylenepiperidine, 3,4 benzpiperidine or 3,5 ethanopiperidine; and pharmaceutically acceptable salts and esters thereof.

The term "loweralkyl" is used herein to mean $C_1$-$C_8$ straight and branched chain radicals, including, but not limited to methyl, ethyl, n-propyl, isopropyl, n butyl, sec butyl, isobutyl, tert-butyl, 2-ethylhexyl, n octyl, 2,4 dimethylpentyl, and the like.

The term "halo" as used herein means fluoro, chloro, bromo or iodo.

The term "loweralkoxy" as used herein means $R_8O$— wherein $R_8$ is a loweralkyl group.

The term "loweralkoxy" as used herein means $R_9CO$— wherein $R_9$ is a loweralkyl group.

The term "aryl" is used herein to mean the aromatic radicals phenyl and naphthyl.

The term "cycloalkyl" as used herein means an aliphatic cyclic group having 3–7 carbon atoms.

The term "arylalkoxyalkyloxy" as used herein means $R_{10}R_{11}$—O—$R_{12}$—O wherein $R_{10}$ is aryl, and $R_{11}$ and $R_{12}$ are loweralkyl.

The term "alkoxyalkyloxy" as used herein means $R_{13}$—O—$R_{14}$—O— wherein $R_{13}$ is $R_{15}$—O—$R_{16}$ wherein $R_{15}$ and $R_{16}$ are loweralkyl or $R_{13}$ is loweralkyl and $R_{14}$ is loweralkyl.

The compounds of the invention include only R epimers at the 9 position. However, the compounds of the invention include both 4″-R and 4″-S epimers.

By "pharmaceutically acceptable" is meant those salts and esters which are, within the scope of sound medical judgment, suitable for use in contact with the tissues of humans and lower animals without undue toxicity, irritation, allergic response, and the like, commensurate with a reasonable benefit/risk ratio, and effective for their intended use in the chemotherapy and prophylaxis of antimicrobial infections.

Preferable heterocyclics include piperidine, morpholine, azepine and aryl substituted piperidine. The most preferable heterocyclic is morpholine.

Preferable compounds include 9 R-morpholino erythromycin A, 9 R piperidino-4″-amino erythromycin A, and 9 R-azepino erythromycin A. The most preferable compound is 9-R morpholino-erythromycin A.

Surprisingly, the compounds of this invention also offer improved in vitro and in vivo antibiotic potency against certain organisms in comparison to erythromycin. Further, these compounds provide an improved therapeutic ratio in comparison to potent erythromycin derivatives of the prior art.

Industrial Applicability

The compounds of the present invention can be used in the form of pharmaceutically acceptable salts derived from inorganic or organic acids. Among the more common pharmaceutically acceptable salts and esters of macrolide antibiotics are the acetate, estolate (lauryl sulfate salt of the propionate ester), ethyl succinate, gluceptate (glucoheptonate), lactobionate, stearate, and hydrochloride forms. Other acid salts used in the pharmaceutical arts are the following: adipate, alginate, aspartate, benzoate, benzene sulfonate, bisulfate, butyrate, citrate, camphorate, camphorsulfonate, cyclopentanepropionate, digluconate, dodecylsulfate, ethanesulfonate, fumarate, gluconate, glycerophosphate, hemisulfate, heptonate, hexanoate, hydrobromide, hydroiodide, 2 hydroxy ethanesulfonate, lactate, maleate, methanesulfonate, 2 naphthalene sulfonate, nicotinate, oxalate, pamoate, pantothenate, pectinate, persulfate, 3 phenylpropionate, picrate, pivalate, propionate, succinate, tartrate, thiocyanate, tosylate, and undecanoate. Although guaternized macrolide compounds are, in general, drastically less active than the parent compound in vivo, basic nitrogen-containing groups can be guaternized with such agents as lower alkyl halides, such as methyl, ethyl, propyl and butyl chloride, bromides and iodides; dialkyl sulfates like dimethyl, diethyl, dibutyl, and diamyl sulfates; long chain halides such as decyl, lauryl, myristyl and stearyl chlorides, bromides and iodides; aralkyl halides like benzyl and phenethyl bromides and others. Water or oil soluble or dispersible products are thereby obtained.

This invention also provides methods of treating and preventing infection by susceptible organisms in a human or lower animal host in need of such treatment, which method comprises administration to the human or lower animal host a therapeutically effective amount of a compound or composition of this invention. The compounds of the present invention may be administered orally, parenterally, by inhalation spray, rectally or topically in dosage unit formulations containing conventional nontoxic pharmaceutically acceptable carriers, adjuvants and vehicles as desired. The term parenteral as used herein includes subcutaneous, intravenous, intramuscular, intraarticular and intrathecal injection and infusion technigues.

Total daily dose of the compounds of this invention administered to a host in single or divided doses may be in amounts, for example, from 0.01 to 50 mg/kg body weight daily and more usually 0.1 to 15 mg/kg body weight daily. Dosage unit compositions may contain such amounts or submultiples thereof to make up the daily dose. It will be understood, however, that the specific therapeutically effective dose level for any particular patient will depend upon a variety of factors including the activity of the specific compound employed, the age, body weight, general health, sex, diet, time of administration, route of administration, rate of excretion, drug combination and the severity of the particular disease undergoing therapy.

This invention also provides pharmaceutical compositions in unit dosage form, comprising an effective amount of a compound of this invention in combination with a conventional pharmaceutical carrier. As used herein, the term "pharmaceutical carrier" means a solid or liquid filler, diluent or encapsulating material. Some examples of the materials which can serve as pharmaceutical carriers are sugars, such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil, safflower oil; sesame oil, olive oil, corn oil and soybean oil; polyols such as propylene glycol, glycerin, sorbitol, mannitol and polyethylene glycol; esters such as ethyl oleate and ethyl laurate; agar; buffering agents such as magnesium hydroxide and aluminum hydroxide; alginic acid; pyrogen-free water; isotonic saline; Ringer's solution, ethyl alcohol and phosphate buffer solutions, as well as other nontoxic compatible substances used in pharmaceutical formulations. Wetting agents, emulsifiers and lubricants such as sodium lauryl sulfate and magnesium stearate, as well as coloring agents, release agents, coating agents, sweetening, flavoring and perfuming agents and preservatives can also be present in the compositions, according to the desires of the formulator. The amount of active ingredient that may be combined with the carrier materials to produce a single dosage form will vary depending upon the host treated and the particular mode of administration.

Injectable preparations such as sterile injectable aqueous or oleagenous suspensions may be formulated according to the known art using suitable dispersing or wetting agents and suspending agents. The sterile injectable preparation may also be a sterile injectable solution or suspension in a nontoxic parenterally acceptable diluent or solvent, for example, as a solution in 1,3 butanediol. Among the acceptable vehicles and solvents that may be employed are water, Ringer's injection, U.S.P. and isotonic sodium chloride solution. In addition, sterile, fixed oils are conventionally employed as a solvent or suspending medium. For this purpose any bland fixed oil may be employed including synthetic and semisynthetic mono-, di- or triglycerides. In addition, fatty acids such as oleic acid find use in the preparation of injectibles.

Suppositories for rectal administration can be prepared by mixing the drug with a suitable nonirritating excipient such as cocoa butter or a polyethylene glycol which is solid at ordinary temperatures but liquid at the rectal temperature and will therefore melt in the rectum and release the drug.

Solid dosage forms for oral administration may include capsules, tablets, pills, powders, prills and granules. In such solid dosage forms, the active compound may be admixed with at least one inert diluent such as sucrose, lactose or starch. Such dosage forms may also comprise, as is normal practice, additional substances other than inert diluents, e.g., tableting lubricants and other tableting aids such as magnesium stearate and microcrystalline cellulose. In the case of capsules, tablets and pills, the dosage forms may also comprise buffering agents. Tablets and pills can additionally be prepared with enteric and other release controlling coatings.

Liquid dosage forms for oral administration may include pharmaceutically acceptable emulsions, microemulsions, solutions, suspensions, syrups and elixirs containing inert diluents commonly used in the art, such as water. Such compositions may also comprise adjuvants, such as wetting agents, emulsifying and suspending agents, and sweetening, flavoring and perfuming agents.

The term "administration" of the antibiotic or composition herein includes systemic use, as by intramuscular, intravenous, intraperitoneal or subcutaneous injection and continuous intravenous infusion, and oral administration thereof, as well as topical application of the compounds and compositions to the site of infection or potential infection.

By "a therapeutically effective amount" of the antibiotic herein is meant a sufficient amount of the compound to treat or prevent susceptible bacterial or other microbial infections, at a reasonable benefit/risk ratio applicable to any medical treatment. Of course, the total daily usage of the compositions herein will be decided by the attending physician within the scope of sound medical judgment. The effective amount of the antibiotic of this invention will vary with the particular organism being treated, the severity of the infection, the duration of the treatment, the specific compound, ester or salt.employed, the age and weight of the patient and like factors well known in the medical arts. In general, treatment and prevention regimens according to the present invention comprise administration to a patient in need of such treatment from about 100 milligrams to about 5,000 milligrams (preferably 500 to 2,000 milligrams) of the compound of this invention per day in multiple doses or, preferably, in a single dose of from about 250 milligrams to about 1,000 milligrams.

In general, the compounds of this invention are synthesized via schematic I and/or II.

Compounds in this invention were synthesized from 9R amino 9-deoxoerythromycin A (a) by reaction of (a) with a reagent such as (b), which typically has a functional group selected from aldehyde, halogen, alkylsulfonate or aryl sulfonate.

Where reagent (b) is functionalized by an aldehyde, the reaction step I, involves a reductive alkylation process wherein catalytic hydrogenation using hydrogen and a catalyst such as palladium may be employed. Alternatively, a homogeneous reductive alkylation reagent such as sodium cyanoborohydride may be employed.

Where reagent (b) is functionalized by a sulfonate or a halogen, the desired compound is prepared by reaction of (a) with the reagent (b) in presence of a base such as triethylamine in a solvent such as acetonitrile. The reaction in this case may be subjected to heating for an appropriate length of time to improve product yields.

Compounds represented by general structure (f) were synthesized by the method described in Scheme II. The starting material (c) from Scheme I is subjected to protection at the 2'—OH group, preferably with an acetate. Subsequent oxidation of the resulting intermediate then occurs at the 4"-position. Introduction of an amino group at that position is achieved through initial conversion of the intermediate to an oxime and its subsequent reduction to the amine.

Scheme I

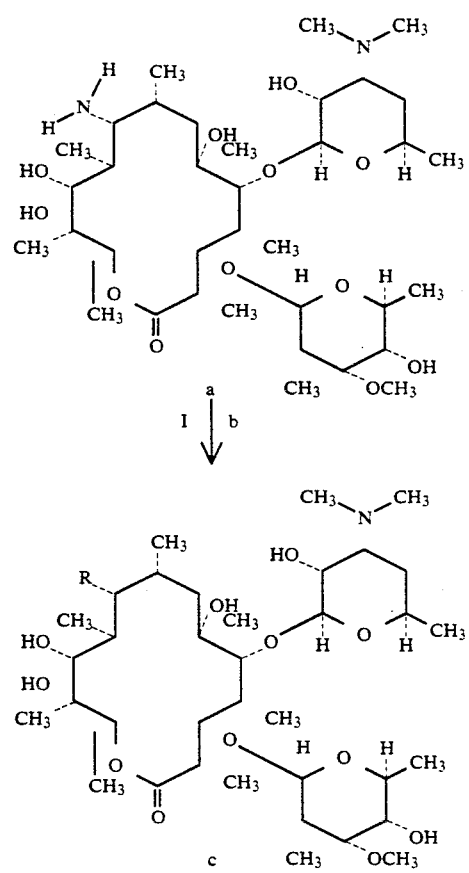

Scheme II

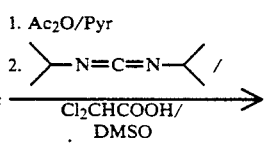

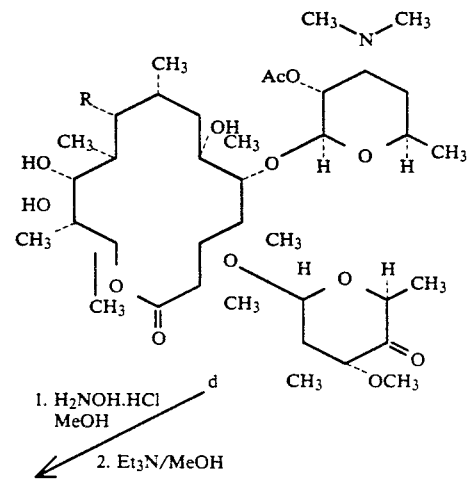

-continued
Scheme II

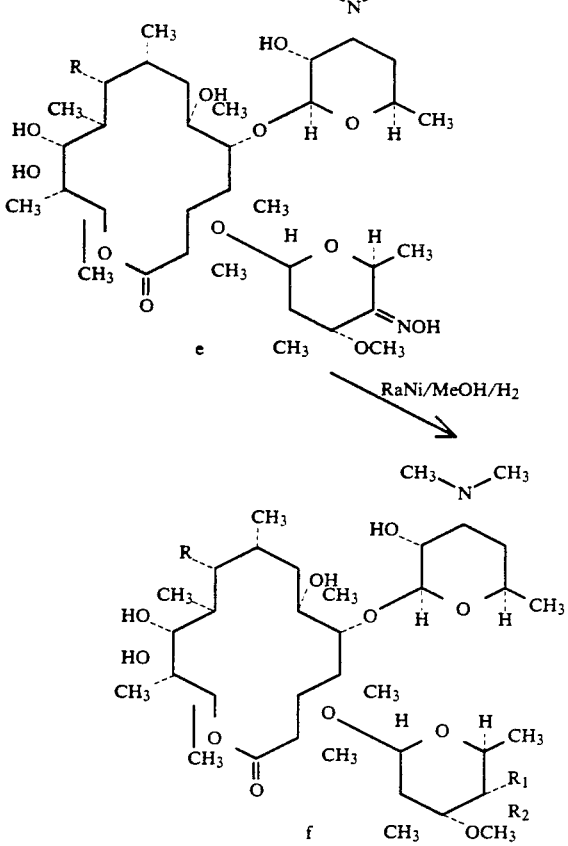

The 4"-amino group can further be subjected to reactions to produce 4"-amino derivatives. Thus, alkylation of compound (f) affords 4"—N-alkyl derivatives as in Examples 33 and 34.

The synthesis Schemes I and II are more particularly described by reference to examples hereinbelow.

Example I(a)

9(R)Erythromycylamine 100 g of erythromycin A 9-oxime was dissolved in 1,500 ml methanol and treated with 200 g Raney Nickel catalyst. The mixture was placed in a Parr Shaker and shaken for 18 hrs under 4 atmospheres of hydrogen pressure. The catalyst was filtered off and washed well with methanol. The clear solution was refiltered through 0.45 u (micron) nylon, and the methanol was removed under reduced pressure. The resulting white foam weighed approximately 93 g. It was dissolved in 600 ml warm acetonitrile and again filtered. After standing at room temperature overnight crystals were harvested, washed with a little ether, and dried to constant mass under reduced pressure at 50° C., yielding 45 g (46%), sufficiently pure/TLC and NMR for use in the examples below. Traces of 9(S) isomer can be removed by a second crystallization from acetonitrile.

Alternatively, 9(R) erythromycylamine can be made in accordance with U.S. Pat. No. 3,652,537 which is incorporated herein by reference.

Example 1

2.0 gm of (a) from Example I(a) was dissolved in 35 ml of acetonitrile followed by addition of 10 ml methanol and 1 ml acetic acid. The reagent 2,2-dimethyl pent 1,5 dialdehyde (1 gm) was added, followed by 250 mg of NaBH$_3$CN. The reaction mixture was stirred for about 1.5 hours at room temperature. The reaction mixture was diluted with 300 ml of 5% aqueous NaH$_2$PO$_4$ and extracted with CHCl$_3$. The aqueous phase was treated with NH$_4$OH and extracted again with CHCl$_3$. The CHCl$_3$ solutions were combined, dried over MgSO$_4$, filtered and the filtrate concentrated by removal of solvent. The crude product was purified by chromatography over silica gel to afford 1.0 gm of Example 1. See Table 1 for structure and physical data.

Example 2

Two grams of (a) from Example I(a) was dissolved in about 20 ml of acetonitrile. To this solution was added 2.4 ml of triethylamine, followed by 2 gm of 1,6 di-0 methanesulfonyl hexan 1,6 diol. This solution was refluxed for 5 to 7 days. The reaction mixture was concentrated by removal of solvent through distillation; and the resulting crude product purified by chromatography over silica gel to yield 0.2 g of Example 2. See Table 1 for structure and physical data.

Example 3

One gram of (a) from Example I(a) was dissolved in 15 ml of toluene. To this solution was added 2.39 ml of N-methylmorpholine, followed by 0.72 ml of 1,4-diiodobutane. The reaction was stirred at 100° C. under nitrogen for 68 hours. The solvent was removed to concentrate the reaction mixture, which was then redissolved in 400 ml ethyl acetate and the organic solution washed with 0.2N NaOH and saturated aqueous NaCl sequentially. The ethyl acetate solution was then dried over MgSO$_4$, concentrated by removal of solvent and the resulting crude product purified by chromatography to afford 730 mg of Example 3. See Table 1 for structure and physical data.

Examples 4–30

Following the synthesis outlined in Example 1 and using the appropriate reactant, other compounds 4–10, 13 and 15–30 as disclosed in Table 1 were made. Following the synthesis outlined in Example 2 and using the appropriate reactant, Examples 11, 12 and 14 disclosed in Table 1 were made.

The structure of each was confirmed by $^1$H NMR, $^{13}$CNMR, elemental analysis and/or high resolution mass spectra as designated.

Examples 31–32

In the same manner as Examples 33–34 are made, Examples 31–32 can be made by using the product of Example 5 instead of the product of Example 19 as the starting material.

Examples 33–34

A solution of 1 gm of the product of Example 19 in 20 ml CH$_2$Cl$_2$ was acetylated by addition of 1 ml of acetic anhydride and stirring at room temperature for about 3 hrs. Solvent was removed and the resulting product redissolved in CHCl$_3$ and washed with NaHCO$_3$. The CHCl$_3$ solution was dried over MgSO$_4$, filtered and solvent removed to yield the 2'—O—acetyl intermediate. The intermediate was redissolved in 9 ml of toluene containing 1 ml of DMSO. 1.1 ml of diisopropyl carbodiimide and 0.11 ml of dichloroacetic acid were added and the mixture stirred for 2 hrs. The mixture was diluted with 100 ml of ethylacetate and washed with NaHCO₃, filtered and concentrated by removal of solvent to yield 580 mg of intermediate (d) after chromatography. Mass Spectrum: m/e 845 (M+H).

A solution of 537 mg of (d) in 20 ml methanol was refluxed for 3 hrs to remove the acetate at the 2'—O—position. To the resulting solution was added 0.27 ml of triethylamine and 133 mg of hydroxylamine hydrochloride. The reaction mixture was stirred at 50° for about 2 days. The mixture was diluted with 100 ml of ethyl acetate and washed sequentially with saturated aqueous NaHCO₃ and saturated NaCl. The organic layer was dried over MgSO₄, filtered and solvents removed. The crude product yielded 330 mg of oxime (e) after chromatography. Mass spectrum: m/e 818 (M+H).

To a solution of 317 mg of (e) in 40 ml of methanol was added 1.28 gm of Raney Nickel. The mixture was shaken under 4 atmospheres of H₂ for 20 hrs. The resulting mixture was filtered and solvent removed to afford the crude products. The mixture was chromatographed to afford 22.1 mg of Example 33 and 10 mg of Example 34. See Table 1 for structure and physical data.

Example 35

To a solution of 0.1 gm. of the product of Example 34, in 15 ml methanol, was added 0.02 ml of formalin and 0.11 gm. of 10% Pd/C. The mixture was hydrogenated at 4 atmospheres and ambient temperature for 2 to 6 hours. The mixture was filtered and solvent removed from the filtrate via distillation, to provide crude Example 35. The crude mixture was purified by column chromatography to afford 0.9 gm. of Example 35.

Example 36

Following the synthesis outlined in Example 35, the compound of Example 36 was made starting from the compound of Example 33.

In vitro Antibacterial Activity

The antimicrobial spectra of a number of compounds of the invention were tested by the following method:

Twelve petri dishes containing successive aqueous dilutions of the test compound mixed with 10 ml of sterilized Brain Heart Infusion agar (Difco 0418-01-5) are prepared. Each plate is inoculated with 1:100 (or 1:10 for slow growing strains, primarily Micrococcus and Streptococcus) dilutions of up to 32 different microorganisms, using a Steers replicator block The inoculated plates are incubated at 35°-37° C. for 20-24 hours. In addition, a control plate, using BHI agar containing no test compound, is prepared and incubated at the beginning and end of each test.

An additional plate containing a compound having known susceptibility patterns for the organisms being tested and belonging to the same antibiotic class as the test compound is also prepared and incubated as a further control, as well as to provide test-to-test comparability. Erythromycin A was used for this purpose.

After incubation, each disk is read. The MIC is defined as the lowest concentration of drug yielding no growth, a slight haze, or sparsely isolated colonies on the inoculum spot as compared to the growth control.

The results are indicated in Tables 2-3.

In vivo Antibacterial Activity

The acute mouse protection test is conducted on ten mice with each of three levels of drug. Mouse mortality is used to calculate an $ED_{50}$ value, i.e., the dose of drug required to protect 50% of the test animals against death due to the inoculum challenge.

The acute mouse protection test is conducted on female, Swiss albino mice, 18-20 grams in weight. The mice are injected intraperitoneally with an 18 hour culture of the indicated test organism diluted sufficiently to provide the desired $LD_{50}$ value. To check the potency of the inoculum, a titration of the indicated test organism is carried out in control animals. The treatment group of animals is dosed with the test compound at 1 and 5 hours post infection and observed for 7 days. The $ED_{50}$ values are calculated using the mortality data collected. Results are indicated in Table 4.

This invention has been described in terms of specific embodiments set forth in detail. It should be understood, however, that these embodiments are presented by way of illustration only, and that the invention is not necessarily limited thereto. Modifications and variations within the spirit and scope of the claims that follow will be readily apparent from this disclosure, as those skilled in the art will appreciate.

TABLE 1

| Example | R* | b | Reaction Type | Typical NMR δ ppm from TMS 3'N(CH₃)₂ | OCH₃ | Mass Spectrum m/z (M + H) |
|---|---|---|---|---|---|---|
| 1 | 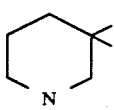 | 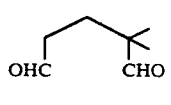 | Ia | 2.29 | 3.32 | 831 |
| 2 |  | 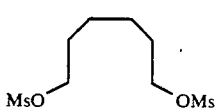 | Ib | 2.28 | 3.33 | 816 |
| 3 | 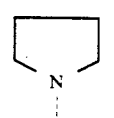 | 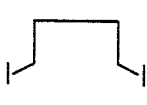 | Ic | 2.29 | 3.37 | 789 |

TABLE 1-continued
| 4 |  | ClCH₂—CHO | Ia | 2.29 | 3.32 | 761 |
| --- | --- | --- | --- | --- | --- | --- |
| 5 |  | OHC~~~CHO | Ia | 2.28 | 3.32 | — |
| 6 | 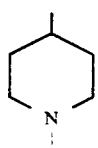 | OHC~CH(CH₃)~CHO | Ia | 2.29 | 3.32 | 817 |
| 7 | 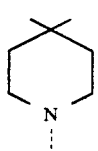 | OHC~C(CH₃)₂~CHO | Ia | 2.29 | 3.32 | 831 |
| 8 | 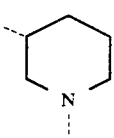 | OHC~CHO (chiral) | Ia | — | — | — |
| 9 | 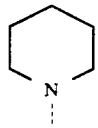 | OHC~~~CHO | Ia | — | — | — |
| 10 | 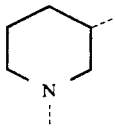 | OHC~~~CHO (chiral) | Ia | — | — | — |
| 11 | 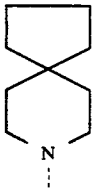 | MsO~C(CH₂)₂~OMs spiro | Ib | — | — | — |
| 12 | 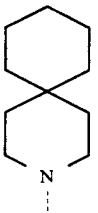 | MsO~C(CH₂)₂~OMs spiro | Ib | 2.31 | 3.32 | 870 |

TABLE 1-continued

| # | Structure 1 | Structure 2 | Type | Val 1 | Val 2 | Val 3 |
|---|---|---|---|---|---|---|
| 13 | 1,2,3,4-tetrahydroisoquinoline (N-substituted) | o-C₆H₄(CHO)₂ (phthalaldehyde) | Ia | 2.30 | 3.33 | 850 |
| 14 | N-substituted pyrrolidine | 1,3-bis(CH₂OMs)cyclopentane | Ia | 2.29 | 3.33 | 828 |
| 15 | piperazine (NH) | (Via deprotection of Compound 18) | | 2.29 | 3.31 | 804 |
| 16 | N-Ac piperazine | AcN(CH₂CHO)₂ | Ia | 2.29 | 3.31 | 846 |
| 17 | N-benzoyl piperazine | PhC(O)N(CH₂CHO)₂ | Ia | 2.29 | 3.31 | 908 |
| 18 | N-Cbz piperazine | PhCH₂OC(O)N(CH₂CHO)₂ | Ia | 2.29 | 3.31 | 938 |
| 19 | morpholine | O(CH₂CHO)₂ | Ia | 2.29 | 3.32 | 805 |
| 20 | thiomorpholine | S(CH₂CHO)₂ | Ia | — | — | — |
| 21 | thiomorpholine S-oxide | O=S(CH₂CHO)₂ | Ia | — | — | — |

TABLE 1-continued

| | | | | | | |
|---|---|---|---|---|---|---|
| 22 | [thiomorpholine 1,1-dioxide, N-substituted] | [O=S(=O)(CH2CHO)(CH2CHO)] | Ia | 2.29 | 3.32 | 853 |
| 23 | [4,4-(ethylenedioxy)piperidine, N-substituted] | [1,3-dioxolane with CH2CHO groups] | Ia | 2.29 | 3.31 | 861 |
| 24 | [4-methoxypiperidine, N-substituted] | [CH(OCH3)(CH2CHO)2] | Ia | — | — | — |
| 25 | [4-hydroxypiperidine, N-substituted] | [CH(OH)(CH2CHO)2] | Ia | — | — | — |
| 26 | [4-phenylpiperidine, N-substituted] | [CH(Ph)(CH2CHO)2] | Ia | — | — | — |
| 27 | [4,4-dimethoxypiperidine, N-substituted] | [C(OCH3)2(CH2CHO)2] | Ia | 2.29 | 3.32 | 863 |
| 28 | [4-oxopiperidine, N-substituted] | [O=C(CH2CHO)2] | Ia | — | — | — |
| 29 | [4-(methoxymethoxy)piperidine, N-substituted] | [CH(OCH2OCH3)(CH2CHO)2] | Ia | — | — | — |
| 30 | [4-(benzyloxymethoxy)piperidine, N-substituted] | [CH(OCH2OBn)(CH2CHO)2] | Ia | — | — | — |

TABLE 1-continued

| Example | R | $R^1$ | $R^2$ | c | Typical NMR δ ppm from TMS $3'N(CH_3)_2$ | $OCH_3$ | Mass Spectrum m/z (M + H) |
|---|---|---|---|---|---|---|---|
| 31 | 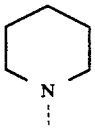 | -NH$_2$ | H | Example 5 | 2.28 | 3.32 | — |
| 32 | 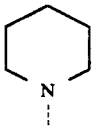 | H | NH$_2$ | Example 5 | 2.29 | 3.33 | — |
| 33 | 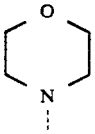 | NH$_2$ | H | Example 19 | 2.28 | 3.29 | 804 |
| 34 | 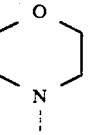 | H | NH$_2$ | Example 19 | 2.28 | 3.30 | 804 |
| 35 | 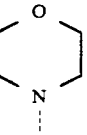 | H | —N(CH$_3$)$_2$ | Example 19 | — | — | — |
| 36 | 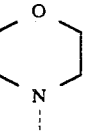 | —N(CH$_3$)$_2$ | H | Example 19 | — | — | — |

*$R_1$ is hydroxy and $R_2$ is hydrogen.
"Bn" as used above means —CH$_2$-phenyl (i.e. benzyl)

TABLE 2

IN VITRO ANTIBACTERIAL ACTIVITY

| Organism | MIC (ug/ml) | | | | | | | |
|---|---|---|---|---|---|---|---|---|
| | 1 | 2 | 3 | 4 | 5 | 6 | 7 | 15 |
| Staphylococcus aureus ATCC 6538P | .39 | .39 | 1.56 | 1.56 | .39 | .39 | .39 | 3.1 |
| Staphylococcus aureus CMX 686B | | 1.56 | | | .39 | | | 6.2 |
| Staphylococcus aureus A5177 | 6.2 | .31 | 25 | 6.2 | 6.2 | 3.1 | 3.1 | >100 |
| Staphylococcus aureus 45 | .39 | .2 | .78 | .78 | .78 | .2 | .2 | 12.5 |
| Staphylococcus aureus 45 RAR 2 | .78 | .39 | 1.56 | 1.56 | .78 | .78 | .39 | 12.5 |
| Staphylococcus aureus 642A | .78 | .39 | | 1.56 | | .39 | .39 | |
| Staphylococcus aureus NCTC 10649 | .78 | .39 | | 1.56 | | .78 | .39 | |
| Staphylococcus aureus CMX 503A | | .39 | 1.56 | | .39 | | | 6.2 |
| Staphylococcus aureus CMX 553 | .78 | .39 | 1.56 | 1.56 | .39 | .39 | .39 | 6.2 |
| Staphylococcus epidermidis 3519 | .78 | .39 | 1.56 | 1.56 | .39 | .39 | .39 | 6.2 |
| Micrococcus luteus ATCC 9341 | .05 | .005 | .39 | .1 | .1 | .05 | =<.05 | 3.1 |
| Micrococcus luteus ATCC 4698 | .1 | 0.1 | .78 | .78 | .2 | .2 | .2 | 12.5 |
| Enterococcus faecium ATCC 8043 | .1 | .02 | .39 | .2 | .1 | .1 | .1 | 12.5 |

TABLE 2-continued

IN VITRO ANTIBACTERIAL ACTIVITY

| Organism | | | | | | | | |
|---|---|---|---|---|---|---|---|---|
| Streptococcus bovis A5169 | .02 | .02 | .1 | .1 | .1 | .02 | =<.05 | 1.56 |
| Streptococcus agalactiae CMX 508 | .1 | .05 | .2 | .2 | .05 | .1 | =<.05 | 1.56 |
| Streptococcus pyogenes EES61 | .1 | .05 | .1 | .2 | .05 | .1 | .1 | 1.56 |
| Streptococcus pyogenes 930 CONST | >100 | >100 | >100 | >100 | >100 | >100 | >100 | >100 |
| Streptococcus pyogenes 2548 INDUC | | 12.5 | 50 | 12.5 | 6.2 | 3.1 | 6.2 | 100 |
| Escherichia coli Juhl | 25 | 0.1 | >100 | >100 | 50 | 12.5 | 12.5 | >100 |
| Escherichia coli SS | .2 | 0.1 | .39 | .78 | .39 | .2 | .2 | 1.56 |
| Escherichia coli DC-2 | 50 | 12.5 | 100 | 100 | 50 | 25 | 12.5 | >100 |
| Escherichia coli H560 | 6.2 | 3.1 | 50 | 25 | 25 | 3.1 | 3.1 | 100 |

| | MIC (ug/ml) | | | | | | | |
|---|---|---|---|---|---|---|---|---|
| Organism | 16 | 17 | 18 | 19 | 22 | 31 | 32 | 33 |
| Staphylococcus aureus ATCC 6538P | 1.56 | 1.56 | .78 | .39 | 3.1 | .78 | .78 | .78 |
| Staphylococcus aureus CMX 686B | 1.56 | | .78 | .39 | | .39 | .78 | |
| Staphylococcus aureus A5177 | 50 | 12.5 | 12.5 | 6.2 | >100 | 6.2 | 6.2 | 6.2 |
| Staphylococcus aureus 45 | 1.56 | .78 | .78 | .39 | 6.2 | .39 | .78 | .39 |
| Staphylococcus aureus 45 RAR 2 | 3.1 | 3.1 | 1.56 | .39 | 6.2 | .78 | 1.56 | .78 |
| Staphylococcus aureus 642A | | 1.56 | | | 6.2 | | 1.56 | .78 |
| Staphylococcus aureus NCTC 10649 | | 1.56 | | | 3.1 | | 1.56 | .78 |
| Staphylococcus aureus CMX 503A | 1.56 | | .78 | .39 | | .78 | | .39 |
| Staphylococcus aureus CMX 553 | 1.56 | 1.56 | .78 | .39 | 3.1 | .39 | .78 | .78 |
| Staphylococcus epidermidis 3519 | 1.56 | 1.56 | .78 | .39 | 6.2 | .78 | .78 | .78 |
| Micrococcus luteus ATCC 9341 | .2 | .2 | .1 | .05 | .39 | .05 | .05 | .05 |
| Micrococcus luteus ATCC 4698 | 1.56 | .78 | .78 | .2 | 3.1 | .39 | .78 | .39 |
| Enterococcus faecium ATCC 8043 | .78 | .39 | .39 | .1 | 1.56 | .2 | .2 | .2 |
| Streptococcus bovis A5169 | .1 | .39 | .05 | .1 | .39 | .02 | .02 | .05 |
| Streptococcus agalactiae CMX 508 | .39 | .2 | .2 | .05 | .39 | .05 | .1 | .1 |
| Streptococcus pyogenes EES61 | .1 | .39 | .1 | .05 | .39 | .05 | .1 | .1 |
| Streptococcus pyogenes 930 CONST | >100 | >100 | 50 | >100 | >100 | >100 | >100 | >100 |
| Streptococcus pyogenes 2548 INDUC | 50 | 25 | 12.5 | 6.2 | 100 | 6.2 | 6.2 | 50 |
| Escherichia coli Juhl | >100 | >100 | >100 | 50 | >100 | 6.2 | 25 | 12.5 |
| Escherichia coli SS | 1.56 | 3.1 | 3.1 | .2 | 1.56 | .2 | .2 | .2 |
| Escherichia coli DC-2 | >100 | >100 | >100 | 50 | >100 | 3.1 | 12.5 | 6.2 |
| Escherichia coli H560 | 50 | >100 | 50 | 6.2 | >100 | 1.56 | 3.1 | 3.1 |

TABLE 3

IN VITRO ANTIBACTERIAL ACTIVITY

| | MIC (ug/ml) | | | | | |
|---|---|---|---|---|---|---|
| Organism | 5 | 6 | 7 | 19 | 27 | 28 |
| Haemophilus influenzae 503B | 0.5 | 1 | 1 | 1 | 1 | .25 |
| Haemophilus influenzae 504 | 1 | 1 | 1 | 4 | 1 | 1 |
| Haemophilus influenzae 519A | 0.5 | .5 | .5 | 2 | .25 | .25 |
| Haemophilus influenzae 566A | 2 | 2 | 2 | 4 | 1 | 2 |
| Haemophilus influenzae 588A | 1 | 1 | 1 | 2 | 1 | 1 |
| Haemophilus influenzae 632A | 1 | 1 | 1 | 4 | 1 | 2 |
| Haemophilus influenzae 667A | 1 | 2 | 1 | 4 | 1 | 1 |
| Haemophilus influenzae 747C | 1 | 1 | 1 | 2 | 1 | .5 |
| Haemophilus influenzae 751 | 4 | 1 | 1 | 8 | 2 | 2 |
| Haemophilus influenzae DILL AMP R | 1 | 1 | 1 | 2 | .5 | .5 |
| Haemophilus influenzae SPK AMP R | 1 | 1 | 1 | 4 | 1 | .5 |
| Haemophilus influenzae SOL AMP R | 1 | 1 | .5 | 2 | 1 | .5 |
| Haemophilus influenzae 1177 | 0.25 | .25 | .25 | .25 | .06 | .25 |
| Haemophilus influenzae 1435 | 0.5 | 1 | .5 | 1 | .25 | .25 |
| Haemophilus influenzae ATCC 9795 | 1 | 1 | 1 | 4 | 1 | 1 |
| Haemophilus influenzae ATCC 19418 | 2 | 2 | 2 | 4 | 1 | 1 |
| Haemophilus influenzae ATCC 10211 | 1 | 1 | 1 | 2 | .5 | 5 |

TABLE 4

| | IN-VIVO MOUSE PROTECTION ASSAY $ED_{50}$ mg/kg | | | | | |
|---|---|---|---|---|---|---|
| | *Staphylococcus aureus* (NCTC 10649) | | *Streptococcus pyogenes* C-203 | | *Streptococcus pneumoniae* (6303) | |
| Example | Oral | Subcutaneous | Oral | Subcutaneous | Oral | Subcutaneous |
| 5 | 41.9 | 7.5 | <7.5 | <0.6 | 4.5 | 0.4 |
| 19 | 44.8 | 15.5 | 9.5 | 2.1 | 9.7 | 1.1 |
| 31 | 125.1 | 25.7 | 27.9 | 0.8 | 13.8 | 1.0 |
| erythromycin | 98.0 | 20.0 | 12.0 | 1.8 | 21.5 | 0.9 |

What is claimed is:

1. A compound of the formula:

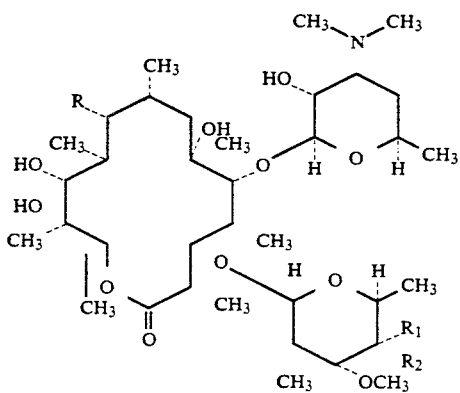

wherein $R_1$ is hydrogen, OH, carbamoyloxy, or $NR_3R_4$ wherein $R_3$ and $R_4$ are independently selected from the group consisting of hydrogen and loweralkyl; $R_2$ is hydrogen when $R_1$ is other than hydrogen or $R_2$ is $NR_3R_4$ as defined above when $R_1$ is hydrogen; and R is a heterocyclic of the formula:

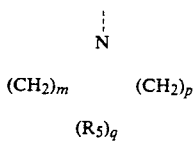

wherein m is 1–3, q is 0 or 1, p is 1–2 and $R_5$ is selected from the group consisting of $CH_2$, —CH=CH—, CH(OH)CH(OH), O, S, NH, C=O, C=S, $SO_2$, SO and $CR_6R_7$ wherein $R_6$ and $R_7$ together form an ethylenedioxy bridge; or R is a heterocyclic as defined above having substituents selected from the group consisting of loweralkyl, hydroxy, loweralkoxy, halo, phenyl, loweralkanoyl, benzoyl, benzyloxycarbonyl, t-butyloxycarbonyl, arylalkoxyalkyloxy and alkoxyalkyloxy; or R is selected from the group consisting of 4,4-tetramethylenepiperidino, 4,4-pentamethylene-piperidino, 3,4-benzpiperidino and 3,5-ethanopiperidino; or pharmaceutically acceptable salts and esters thereof.

2. The compound of claim 1 wherein R is an optionally substituted moiety selected from the group consisting of piperidino, morpholino and azepino, where the substituents are as defined in claim 1.

3. The compound of claim 1 wherein R is selected from the group consisting of morpholino, piperidino, phenyl-substituted piperidino and azepino.

4. The compound of claim 3 wherein $R_1$ and $R_2$ are different and are selected from the group consisting of hydrogen and amino.

5. 9-R-morpholino-erythromycin A.

6. 9-R-piperidino-4"-amino-erythromycin A.

7. 9-R-azepino-erythromycin A.

8. A pharmaceutical composition in unit dosage form, comprising a therapeutically effective amount of a compound according to claim 1 in combination with a pharmaceutical carrier.

9. A method of treating bacterial infections in humans and lower animals in need of such treatment, comprising administering to the human or lower animal a therapeutically effective amount of the composition of claim 8.

* * * * *